US 11,915,464 B2

(12) United States Patent
Donner

(10) Patent No.: US 11,915,464 B2
(45) Date of Patent: Feb. 27, 2024

(54) METHOD AND A SYSTEM FOR CREATING A MEDICAL IMAGE DATABASE BY MEANS OF A CONVOLUTIONAL NEURAL NETWORK

(71) Applicant: CONTEXTFLOW GMBH, Vienna (AT)

(72) Inventor: Rene Donner, Vienna (AT)

(73) Assignee: contextflow GmbH, Vienna (AT)

(*) Notice: Subject to any disclaimer, the term of this patent is extended or adjusted under 35 U.S.C. 154(b) by 858 days.

(21) Appl. No.: 16/464,167

(22) PCT Filed: Nov. 23, 2017

(86) PCT No.: PCT/AT2017/060312
§ 371 (c)(1),
(2) Date: Aug. 21, 2020

(87) PCT Pub. No.: WO2018/094438
PCT Pub. Date: May 31, 2018

(65) Prior Publication Data
US 2020/0411164 A1 Dec. 31, 2020

(30) Foreign Application Priority Data
Nov. 25, 2016 (AT) .............................. A 51072/2016

(51) Int. Cl.
G06V 10/44 (2022.01)
G16H 30/20 (2018.01)
(Continued)

(52) U.S. Cl.
CPC ............ G06V 10/454 (2022.01); G06F 16/51 (2019.01); G06F 16/583 (2019.01);
(Continued)

(58) Field of Classification Search
CPC ........ G16H 30/20; G16H 30/40; G06F 16/51; G06F 16/583; G06F 16/5866;
(Continued)

(56) References Cited

U.S. PATENT DOCUMENTS 6,760,714 B1 7/2004 Caid et al.
8,965,891 B1 * 2/2015 Bengio .................. G06F 18/24
707/913
(Continued)

FOREIGN PATENT DOCUMENTS

CN 106037710 A * 10/2016 ............. A61B 5/026

OTHER PUBLICATIONS

Hofmanninger et al, Mapping Visual Features to Semantic Profiles for Retrieval in Medical Imaging, 2015, IEEE Computer Vision Foundation, pp. 457-465. (Year: 2015).*
(Continued)

Primary Examiner — Aaron W Carter
Assistant Examiner — Kathleen M Broughton
(74) Attorney, Agent, or Firm — Christensen, Fonder, Dardi & Herbert PLLC

(57) ABSTRACT

Embodiments of the disclosure are directed to methods and systems for creating a medical image database, wherein data which comprise partial images of two-dimensional or higher-dimensional initial images of parts of the human body are created, a projection for obtaining feature vectors is created from the partial images, wherein, in order to prepare the execution of the projection, a neural network based on specified learning partial images is created, wherein the data records are used within the scope of a metric learning method to learn the projection and creation of the feature vectors from learning partial images. This is achieved for example by specifying learning partial images that are slightly shifted, rotated, skewed or stretched relative
(Continued)

to one another and were created starting from the same initial image as similar.

12 Claims, 3 Drawing Sheets

(51) Int. Cl.
*G16H 30/40* (2018.01)
*G06N 3/08* (2023.01)
*G06F 16/51* (2019.01)
*G06F 16/58* (2019.01)
*G06F 16/583* (2019.01)
*G06V 10/82* (2022.01)

(52) U.S. Cl.
CPC ........... *G06F 16/5866* (2019.01); *G06N 3/08* (2013.01); *G06V 10/82* (2022.01); *G16H 30/20* (2018.01); *G16H 30/40* (2018.01); *G06V 2201/031* (2022.01)

(58) Field of Classification Search
CPC ................ G06F 16/24578; G06N 3/08; G06V 10/454; G06V 10/82; G06V 2201/031; G06K 9/6215
See application file for complete search history.

(56) References Cited

U.S. PATENT DOCUMENTS

| | | | |
|---|---|---|---|
| 2004/0165767 A1 | 8/2004 | Gokturk et al. | |
| 2004/0249774 A1* | 12/2004 | Caid | G06V 10/451 706/14 |
| 2007/0055153 A1* | 3/2007 | Simopoulos | G16H 30/40 600/437 |
| 2014/0079297 A1* | 3/2014 | Tadayon | G06V 40/172 382/118 |
| 2015/0161786 A1* | 6/2015 | Seifert | A61B 6/5205 382/119 |

OTHER PUBLICATIONS

Wu et al, Online Multi-Modal Distance Metric Learning with Application to Image Retrieval, 2016, IEEE Transactions on Knowledge and Data Engineering, 28(2): 454-467. (Year: 2016).*

Bashiri et al, Multi-Modal Medical Image Registration with Full or Partial Data: A Manifold Learning Approach, 2018, MDPI Journal of Imaging, 5(5) pp. 1-24. (Year: 2018).*

Bengio, Yoshua et al., "Representation learning: A review and new perspectives," *IEEE Transactions on Pattern Analysis and Machine Intelligence*, vol. 35, No. 8, pp. 1798-1828 (2013).

Goodfellow, Ian, et al., "Generative Adversarial Nets," *Advances in Neural Information Processing Systems*, 9 pages (2014).

Sundermeyer, Martin, et al., "LSTM Neural Networks for Language Modeling," *Thirteenth Annual Conference of the International Speech Communication Association*, 4 pages (2012).

Vaswani, Ashish, et al., "Attention is All You Need," arXiv preprint arXiv:1706.03762, 15 pages (2017).

Dai, Andrew M., et al., "Document embedding with paragraph vectors," arXiv preprint arXiv:1507.07998, 8 pages (2015).

Han, Xufeng, et al., "Matchnet: Unifying Feature and Metric Learning for Patch-Based Matching," *2015 IEEE Conference on Computer Vision and Pattern Recognition (CVPR)*, pp. 3279-3286 (Jun. 7, 2015).

Prasoon, Adhish, et al., "Deep Feature Learning for Knee Cartilage Segmentation Using a Triplanar Convolutional Neural Network," *ECCV 2016 Conference;* [*Lecture Notes in Computer Science*, Springer International Publishing, CHAM, pp. 254-261 (Sep. 22, 2013).

* cited by examiner

US 11,915,464 B2

METHOD AND A SYSTEM FOR CREATING A MEDICAL IMAGE DATABASE BY MEANS OF A CONVOLUTIONAL NEURAL NETWORK

PRIORITY CLAIM

The present application is a National Phase entry of PCT Application No. PCT/AT2017/060312, filed Nov. 23, 2017, which claims priority from Austrian Patent Application A51072/2016, filed Nov. 25, 2016, the disclosures of which are hereby incorporated by reference herein in their entirety.

BACKGROUND

The invention relates to a method and a system for creating a medical image database according to the embodiments of the disclosure. In particular, the invention relates to the technical field of image processing, in particular medical image processing, for example of medical image data resulting from imaging diagnostic methods. This data is constituted for example by two-dimensional or three-dimensional CT or MIII images, ultrasound images, or microscopic images. Preferred aspects of the invention also relate to methods for processing medical texts, such as specialist journals and written diagnosis texts, patient reports, etc.

SUMMARY

The main challenges in this field lie in the identification of the features relevant for the diagnosis. These features make it possible to reliably support the doctor in question.

Particularly in the medical field, the search for image data, such as x-ray images or computed tomography images, which show similar anatomical structures, changes, or symptoms of disease and therefore can be associated with similar cases of disease, is very difficult and time-consuming, in particular if only visual information is available as the basis for the search, since often only small-area changes are produced in the human body.

In the clinical field however, a precise search for similar image data that can be carried out quickly, even in comprehensive medical databases, is desirable so as to ascertain similar cases of disease as quickly as possible for a current case of disease and, proceeding from this basis, make a diagnosis for the current case of disease.

An object of the invention is therefore to provide a method for efficiently creating medical image databases, so that these databases can be searched precisely and quickly. In particular, an object of the invention is to perform an image search on the basis of content-related criteria. It is advantageous in this regard if modern deep-learning methods, such as convolutional neural networks (CNN), or recurrent neural networks (RNN) can be utilised for this purpose.

Aspects of the invention achieve this object by a method for creating a medical image database, wherein a) data records which comprise partial images of two-dimensional or higher-dimensional initial images of parts of the human body are specified, and wherein preferably for each partial image of an initial image, the corresponding position in the initial image is known, and/or the individual initial images or partial images are provided with additional information as appropriate, a partial image can also correspond to an entire initial image.

In accordance with aspects of the invention it is provided here that b) a projection for obtaining feature vectors is created from the partial images, which projection, in particular visually or semantically, maps similar partial images to feature vectors with a short distance, and wherein, in order to prepare the execution of the projection, a neural network, in particular a convolutional neural network, based on specified learning partial images, is created, wherein the data records or part of the data records are/is used by the neural network within the scope of a metric learning method to learn the projection and creation of the feature vectors from learning partial images or groups of learning partial images and a specified similarity, that is to be achieved, between the learning partial images, wherein one or more of the following specifications forms/form the basis of the relevant metric learning method:

specification of n-tuples of learning partial images or groups of learning partial images that are slightly shifted, rotated, skewed or stretched relative to one another and were created starting from the same initial image as similar; and/or specification of n-tuples of learning partial images or groups of learning partial images that were created starting from the same sub-region of the initial image as similar, wherein at least one of the learning partial images is modified in relation to the sub-region of the initial image in such a way that the learning partial images have different noise and/or different image intensity and/or different contrast, and/or specification of n-tuples of sub-regions originating from the same initial image or groups of initial images as learning partial images, wherein the similarity to be achieved between the learning partial images in question of the n-tuple is dependent on the spatial distance of the relevant sub-regions in the initial image, wherein in particular learning partial images are considered to be all the more similar, the closer the sub-regions in question are arranged to one another in the initial image, and/or creation of a compressed representation of the information contained in a partial image learning partial images or groups of learning partial images from the same initial image 4a, 4b, 4c or from different initial images 4a, 4b, 4c, which are to be considered similar due to external features, such as text-based, numerical or semantic information, stored with the corresponding initial images 4a, 4b, 4c.

In accordance with further aspects of the invention it is provided that c) wherein the projection is applied to the partial images of the data records and/or to a number of further partial images of further data records, and at least one feature vector is obtained accordingly for each of these partial images, and d) wherein the feature vectors created in this way, in particular linked with the initial images and/or data records or further data records, are stored in an index data structure.

Aspects of the invention are of particular advantage because—for example for radiologists—it is possible with the image database thus created to find, for a specified medical image or partial image, similar partial images stored in the created database which are provided with additional information as appropriate. Furthermore, similar cases of partial images which—for example for radiologists—contain improved information can also be extracted from the database.

For example, in order to also efficiently store information from the medical records of a patient in the database, it can be provided that additional information is stored in the data records, wherein the additional information is specified as text information and/or semantic information and/or numerical information and that, optionally with the presence of text information or numerical information, the text information or numerical information is stored in the databases in the form of tags and/or semantic representations.

In order to be able to obtain feature vectors which can be searched particularly precisely and quickly from the partial images, it can be provided that the additional information is used by the neural network for creation of the projection, wherein the projection is created in such a way that learning partial images which originate from initial images or correspond to partial images associated with the same additional information are specified as similar.

A particularly quick and effective search in the database for image data of cases of disease affecting certain body parts is made possible if the particular position of the partial images of an initial image based on the human body is determined, wherein in particular the information regarding the position of the partial images is used by a neural network to learn a projection for estimating the positions of partial images. In various embodiments the projection is learned with the target function that, by mapping pairs or groups of partial images, the spatial constellation of the pairs/groups before and after the projection is similar and/or wherein the projection is learned based on a known mapping of partial images to positions (for example from registration processes). In various embodiments, in addition to the feature vectors, the learned or known position information is stored in the database wherein, in the presence of a search request, the searched position in the body is determined and the database is searched for feature vectors of partial images for which the same position is stored in their data records or the position of which does not exceed a threshold value, specified by the user, for a distance from the searched position.

In order to carry out in the database a precise, computing-power-efficient search for image data regarding certain cases of disease, it can be provided that, in order to create a search request, the user specifies text information, numerical information and/or semantic information, that optionally, the text information or numerical information is converted into tags and/or semantic representations, that, in the presence of a search request, the database is searched for feature vectors which have similar tags and/or semantic representations, and that, in order to create a search request, at least one query image, in particular of a region of interest, is selected from at least one two-dimensional or higher-dimensional examination image or in an examination image sequence.

In various embodiments a feature vector according to the learned projection is determined for the query image after the projection is applied to the partial images of the data records and/or to a number of further partial images of further data records, and at least one feature vector is obtained accordingly for each of these partial images.

In various embodiments the database is searched for data records with feature vectors that lie in the vicinity of the feature vector of the query image on the basis of a specified metric, and data records of which the partial images look similar to the selection region or are semantically relevant are output as the result of the search request.

In order to be able to perform a search in a database comprising two-dimensional image data starting, for example, from three-dimensional image data as well, it can be provided that, by creating a section, a dimension-reduced query partial image also of reduced dimensions as appropriate is created in order to search similar images for an examination image or an examination image sequence, and said query partial image is used for the search request.

In order to keep the number of search results as low as possible so that only the search results that are most relevant for the user are determined and output, it can be provided that, when searching the similar feature vectors in the database, search results are excluded on account of the tags and/or semantic representations stored in the associated data records in the database, in particular that search results are excluded on the basis of criteria specified by the user for the tags and/or semantic representations, and/or that a ranking of the determined data records in accordance with their similarity to or conformity with the tags and/or semantic representations of the search request and/or in accordance with their similarity, and/or the similarity determined by the distance of the relevant feature vectors, to at least one query image of the search request is created and output is the result of the search request.

So that a user can be provided not only with image data, but also additional information or statistical data as the result of the search request, it can be provided that the text information stored in the relevant data records in the form of tags, numerical information and/or the semantic information stored in the form of semantic representations is output as the result of the search request and/or that the tags of the partial images similar to the selection region are statistically evaluated and the statistical result is output.

In order to ensure the protection of patient data, for example if a search request by a user is transmitted over the Internet to the database, it can be provided that the examination images and/or examination image sequences and/or text information and/or numerical information and/or semantic information forming the basis of the search request is anonymized before the search request is transmitted by the user to the database.

In order to prepare the results, determined as a result of a search request, in a structured manner for the user, it can be provided that, without a search request, groups of partial images and/or text information and/or numerical information and/or semantic information with similar feature vectors are created and output directly in the database on account of the data provided in the database, and as appropriate additional information in respect of these groups is output, and/or that, in response to the search request of a user, adjacent groups in the database of partial images and/or text information and/or numerical information and/or semantic information with similar feature vectors are determined and output, and as appropriate additional information in respect of these groups is output.

In order to be able to carry out a cascade-like search successively in a plurality of databases, wherein each further search request builds on the search results already determined, it can be provided that the search results determined as the result of a first search request to the database, in particular partial images, group information, text information, numerical information and/or semantic information, is used in order to create at least one further search request, and that the further search request is transmitted to at least one further database, and/or that in order to create the at least one further search request to the at least one further database, further information output as the result of the first search request to the database is used. In various embodiments in particular output statistical results and/or initial images and/or similar partial images are used, wherein the dimension of the output initial images and/or the output partial images is reduced as appropriate for the further search request in the at least one further database.

For particularly precise creation of a search request with inclusion of search results of a database to which the user does not have direct access, it can be provided that individual data records of the database are used exclusively for the formation of a projection function, but are not provided to the user for inspection as results of queries.

In order to be able to also use initial or partial images of which the pixel or voxel dimensions are unknown in order to create the database or in order to create a search request to the database, it can be provided that size details regarding the pixel dimensions or voxel dimensions of the initial images or partial images are stored in the data records, or that for the initial images or partial images the pixel dimensions or voxel dimensions are predefined by searching for similar reference initial images or reference partial images, originating in particular from the same body part, with known pixel or voxel dimensions. In various embodiments a scaling is then sought by image comparison, by means of which scaling the initial image or partial image can be brought optimally into conformity with the reference initial image or reference partial image, and proceeding from this scaling and the known pixel dimensions or voxel dimensions of the reference initial image or reference partial image, the pixel dimensions or voxel dimensions of the initial image or partial image are determined and stored in the database.

In a preferred embodiment of the invention, images can be found that are similar to a specified search image. In a further advantageous embodiment of the invention, images that are relevant for a query are learned on the basis of a target similarity learned by training, wherein this target similarity can be learned by training on the basis of known images. In particular, a distance function specifying a distance between two images can also be learned by training.

A further advantageous embodiment of the invention enables an improved determination of a distance function between two images on the basis of an improved data foundation comprising information regarding the relevant patient, curves, diagnoses, data regarding the progression of the disease, prognoses, and image data. Here, after the training, an approximate target similarity can be determined on the basis of part of the data, for example merely on the basis of the biomedical image data. This target similarity can be used in order to later create diagnoses or prognoses regarding the progression of the disease. This embodiment of the invention is additionally able to create a distance function that determines the essential characteristics of the target similarity also on the basis of data provided only partially, such as in particular exclusively on the basis of the image data.

In a preferred embodiment of the invention it is also possible to create training on the basis of similarity or distance functions, and the creation or obtainment of an index exclusively based on CNNs for image processing and RNNs for text processing.

A further advantage of preferred embodiments of the invention is the discovery of relevant cases, patients or patient data on the basis of available image information of an initial case or query case, wherein, at the time of the query, only an image is available to the user as a basis for the search. A direct association between similar cases usually can be modelled only with a great deal of difficulty on account of semantic differences in the data.

In a preferred embodiment of the invention a distance function can be determined for the ranking of search results on the basis of a search region within the image specified by the user, optionally in combination with further patient information, such as age or sex.

In a further embodiment of the invention, the results of greatest relevance for the user or the most highly ranked results are presented visually. These results can be confirmed by the user on the basis of his/her experience.

It is particularly advantageous that individual embodiments of the invention can learn a large number of relationships, create an index, determine a distance function, and learn statistical evaluations and modellings on the basis of data that are created during day-to-day operation of a hospital, without the need to perform manual annotation for this purpose.

It is also particularly advantageous that in individual embodiments of the invention additional data sources, such as specialist articles, recordings, images and displays, teaching materials and similar additional information can be included in the search, and therefore the diagnosis and assessment can be significantly facilitated. This is made possible in particular by the simple use of a data model that has been obtained on the basis of a large amount of data created during day-to-day operation of the hospital. It is also possible that a search or assessment is performed on account of a query image based on a broad data basis; however, the individual data records forming the basis of the database do not need to be displayed, since in particular exclusively other data records can be accessed.

A further preferred embodiment of the invention uses 2D, 3D or higher-dimensional images, for example radiological images, CT images or MR images, in order to provide the user visually with similar medically relevant cases from a database belonging to the hospital.

A further embodiment of the invention uses, for the training, the available semantic information associated with the individual diagnostic reports. An automated full-text search in medical literature can also be used.

A further preferred embodiment of the invention relates to a system for, in particular simultaneous, searching of medical image data, medical text information and semantic information proceeding from a search request of a user consisting of an image and a region of interest. The region of interest may also comprise the entire image. The system determines a ranking of relevant data records as the result of the search request. Data records that are of greater relevance or that are more similar to the image are ranked more highly than data records of lower relevance or lower similarity.

Data records usually consist of:
medical image data, for example, but not exclusively, computed tomography or magnetic resonance tomography image data,
medical text information, for example, but not exclusively, radiological reports, medical websites, publications, literature, didactic information sources, or other material,
semantic information, for example, but not exclusively, marked sub-regions of examination images and semantic information from clinical texts.

In order to carry out the individual operations, the system has an indexing unit, learning unit, and a search unit. An indexing unit and a learning unit are preferably trained with data from different regions, such as (1) medical image data, for example, but not exclusively, computed tomography or magnetic resonance tomography image data, and at the same time (2) image data from documents, for example, but not exclusively, websites, publications, literature, didactic information sources, or other material, and at the same time (3) semantic information.

The indexing unit and the learning unit are preferably additionally trained with patient-specific data, such as radiological reports and semantic information from radiological reports.

It is particularly advantageous if the learning unit and the indexing unit use semantic markers or text information from one domain as additional cost terms in the training and indexing of data of another domain.

It is also advantageous if the learning unit focuses implicitly on sub-regions of image data that are semantically expedient, such as partial images proceeding from data of another domain, such as computed tomography or magnetic resonance tomography volumes.

It is also advantageous if, in addition, the learning unit can determine the scale of image data in one domain on the basis of known scales in another domain, even if the physical size or resolution in the first domain is unknown. The indexing unit additionally indexes the determined scales jointly with the image data.

Lastly, it is advantageous if the learning unit can train a CNN which maps blocks in a common spatial reference frame, wherein the resultant model can be used in order to map individual blocks in the reference frame, but also in order to map entire volumes in this reference frame and in this way register the image data.

It can furthermore be provided advantageously that the learning unit can estimate a position, in particular of specific image portions to be determined, by means of CNNs, wherein in addition the indexing unit indexes the estimated position jointly with the image data, or wherein the search unit automatically determines the position of a query image and the positions in the query image in an anatomical reference system, whereby the display and further use, for example for an enrichment of the search request, of reference coordinates, or names of anatomical structures, or illustrations of anatomical structures as the result of the search request is made possible.

It is furthermore advantageous if the learning unit, under specification of a word or a plurality of words, can make predictions in respect of the likelihood that one of a series of semantic terms or identifiers that are given in a terminology or ontology, such as RadLex, MESH, Snomed or other, is present.

It is furthermore advantageous if the learning unit, under specification of a word or a plurality of words, trains an RNN to predict the likelihood of said word/plurality of words representing one of a series of semantic identifiers of specialist medical terms. In addition, a score can be trained and it can be predicted whether these identifiers are specified for example as "absent", "sparse" or "present". The training can advantageously additionally combine a prediction-cost function with additional cost function in order to model word or symbol sequences.

The partial images do not necessarily have to be sections or blocks and also might not have a cubic or rectangular shape, for example might have a circular or spherical shape.

The indexing unit preferably stores a compact representation of the partial image, section or block of each image in addition to the metadata for additional information, such as patient age, block position, semantic information, in a data structure optimized for quick searching.

The search unit advantageously uses the index in order to find the most similar results, wherein, if desired, metadata can be used as limitations in the search.

A further advantageous development of embodiments of the invention provides that the data structure is used in the indexing unit in order to search the indexed data structures, for example in order to find clusters in the data or metadata.

It can also be provided advantageously that the indexing unit stores indices of the terms or text information in the form of paragraph vectors or word vectors.

The indexing unit advantageously learns filters that can be separated low-dimensionally and processes these in order to increase the search speed.

It can be provided particularly advantageously that the search unit connects indices of image data and text data and semantic data.

It can be provided particularly advantageously that the search unit determines a result of ranked relevant data records or cases, so that data records of greater relevance or greater similarity are ranked more highly than data records of lower relevance or lower similarity, wherein the ranking of a projection (representation function) that takes into consideration relevant semantic similarity, even if it receives only the image and an ROI as input information, is defined, wherein the projection (representation function) is based on CNNs and RNNs, which are trained by a cost function oriented towards the relative position and/or a half-monitored cost function a weakly monitored cost function.

It is furthermore also possible to advantageously cascade the method according to embodiments of the invention in order to obtain additional information within the scope of the cascade.

It can be provided advantageously that the search unit enriches a search request of a user with the results of search requests in different indexes of different domains, for example with images or text information or semantically, in order to perform a subsequent search request. This search may deliver relevant or more relevant information, in particular if it is used for the creation of further requests.

Lastly, it can be provided that the search data provided by the user or a further system are anonymized in the browser prior to the transfer of the data.

Further advantages and embodiments of the invention will become clear from the description and the accompanying drawings. Particularly advantageous exemplary embodiments of the invention, which are not to be understood as limiting however, will be presented schematically hereinafter on the basis of the accompanying drawings and will be described in exemplary fashion with reference to the drawings.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
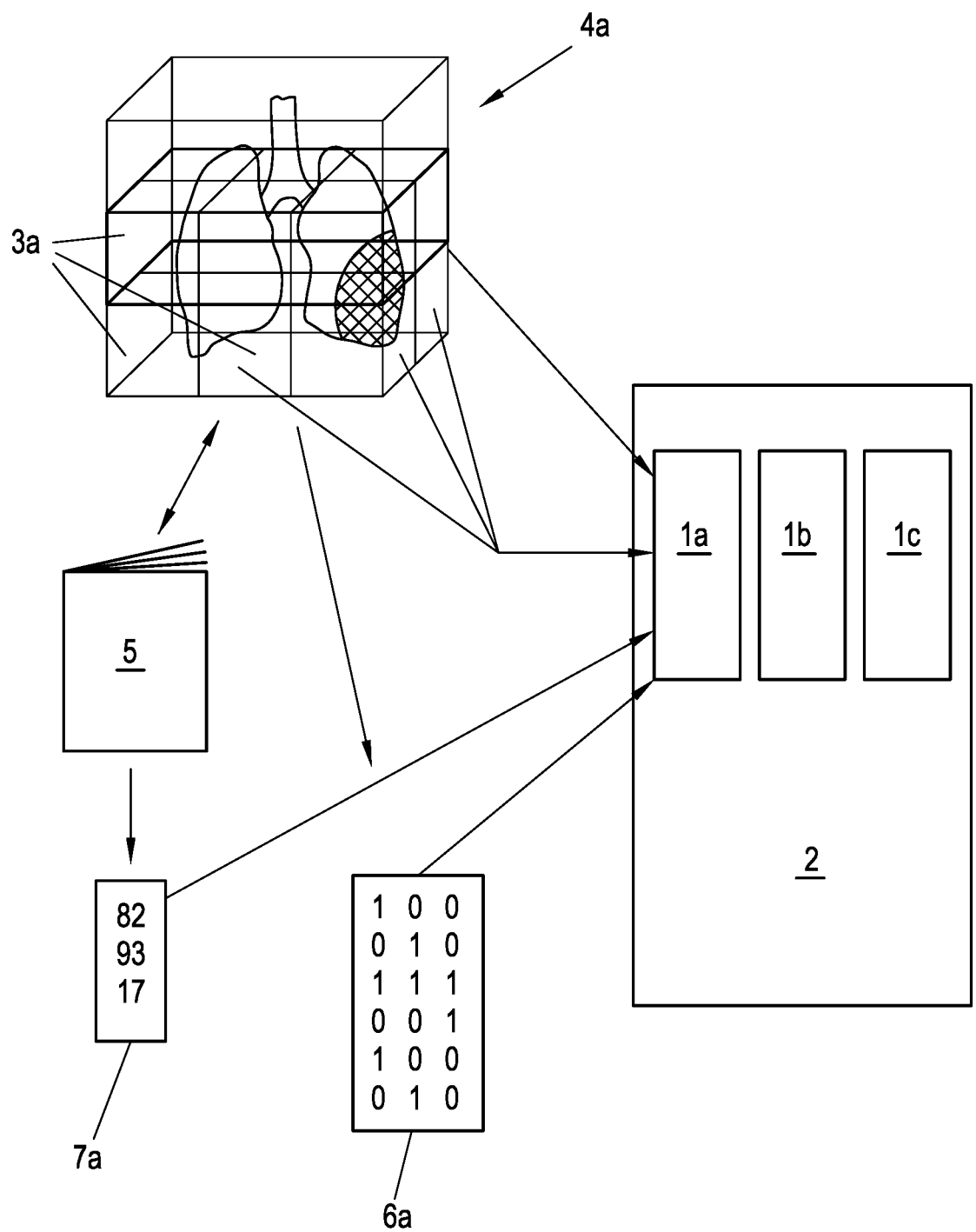
FIG. 1 shows schematically the creation of a data record in a database.

While the embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

Creation of a Database Containing Medical Image Data

FIG. 1 shows a schematic depiction of a database 2 containing medical image data, which for example are recorded in a hospital during the examination of patients. The database 2 is accessible on a server in the hospital or on the Internet and in FIG. 1 contains a plurality of data records 1a, 1b, 1c, wherein each data record 1a, 1b, 1c comprises partial images 3a, 3b, 3c of two-dimensional or higher-dimensional initial images 4a, 4b, 4c of parts of the human body (see FIG. 2).

In order to create the database 2, medical image data, for example such as images obtained by radiological processes or magnetic resonance processes, are firstly predefined as initial images 4a, 4b, 4c. This image data is constituted for example by two-dimensional x-ray images, solid graphic image data, or data from imaging microscopy processes, but also by three-dimensional x-ray or magnetic resonance tomography images or four-dimensional contrast agent image sequences. In the initial images 4a, 4b, 4c, large numbers of sub-regions are selected, for example by displacing a pixel grid along the initial image in question 4a, 4b, 4c, wherein the selected sub-regions are stored as partial images 3a, 3b, 3c in the data records 1a, 1b, 1c of the database 2. Due to the selection of partial images 3a, 3b, 3c, for example by the systematic displacement of a pixel grid along the initial image 4a, 4b, 4c in question, the position thereof in the initial image 4a, 4b, 4c is also known, and in each case for example 100,000 partial images 3a, 3b, 3c are selected from an initial image 4a, 4b, 4c. A partial image 3a, 3b, 3c however may also correspond to a total initial image 4a, 4b, 4c.

Figure 2:
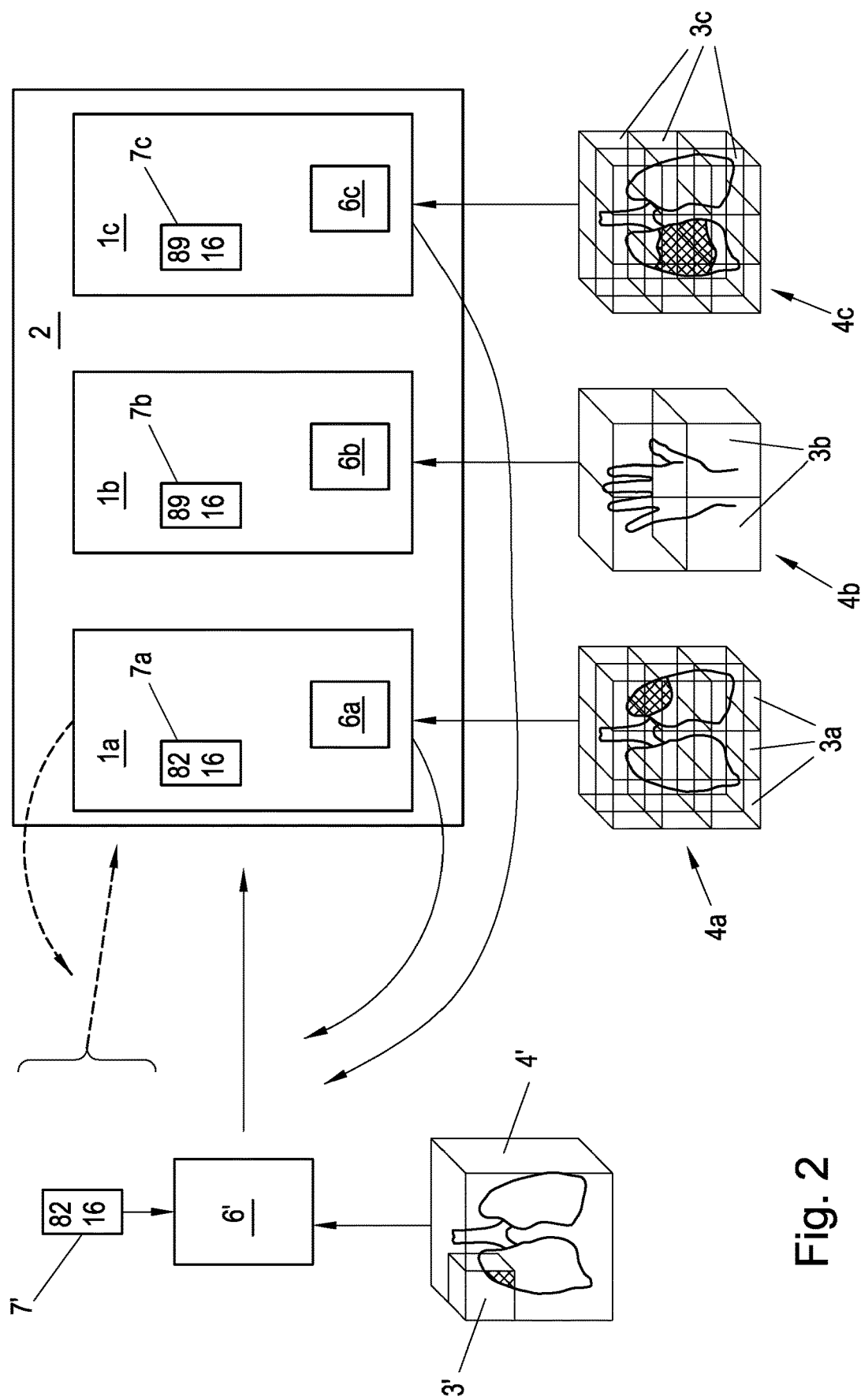
FIG. 2 shows schematically a search request to the database from FIG. 1.

The initial image 4a of the data record 1a shown in FIG. 1 is a three-dimensional computed tomography image of the lungs of the patient. Here, it can be seen in the initial image 4a of the data record 1a that a sub-region of the right lobe of the lung of the patient contains changes. The initial images 4b, 4c and the partial images 3b, 3c, selected thereof, of the data records 1b, 1c which are likewise stored in the database 2 shown schematically in FIG. 1 are shown in FIG. 2.

When creating the database 2, a projection for obtaining feature vectors 6a, 6b, 6c from the partial images 3a, 3b, 3c is created for a memory-space-saving design and/or for rapid searchability of the database 2 for content-relevant partial images. Here, the projection, in particular visually or semantically, maps similar partial images 3a, 3b, 3c to similar feature vectors 6a, 6b, 6c, and when applied to a partial image 3a, 3b, 3c delivers a feature vector 6a, 6b, 6c, wherein in particular the number of entries of a particular feature vector 6a, 6b, 6c is lower than the number of pixels of partial images 3a, 3b, 3c.

This reduction of the entries of a feature vector 6a, 6b, 6c in comparison to the number of the pixels of a partial image 3a, 3b, 3c leads advantageously to a quicker searchability of the database 2. Instead of a time-consuming and processing-power-intensive searching of the database 2 for similar initial images 4a, 4b, 4c or partial images 3a, 3b, 3c of the initial images 4a, 4b, 4c, a search for similar feature vectors 6a, 6b, 6c representing the partial images 3a, 3b, 3c or initial images 4a, 4b, 4c is sufficient. Furthermore, this projection makes it possible to map partial images 3a, 3b, 3c that look different, but with which, however, similar semantic information is stored, for example, by the same hospital, to similar feature vectors, which will be explained hereinafter in even further detail. Partial images 3a, 3b, 3c in which for example the mapped tissue has changes of different visual appearance, but which can be associated with the same disease are thus also mapped to similar feature vectors 6a, 6b, 6c.

In order to prepare the execution of the projection, a neural network, in particular a convolutional neural network, is created on the basis of specified learning partial images by a training unit. The data records 1a, 1b, 1c or part of the data records 1a, 1b, 1c are/is used by the neural network within the scope of a metric learning method in order to learn the projection and the creation of the feature vectors 6a, 6b, 6c from learning partial images and a predefined similarity, that is to be achieved, between the learning partial images.

In order to effectively learn the projection or the creation of the feature vectors 6a, 6b, 6c, n-tuples of learning partial images or groups of learning partial images of one or more of the following types are specified as similar by the relevant metric learning method:

learning partial images which are slightly shifted, rotated, skewed or stretched relative to one another and are created proceeding from the same initial image 4a, 4b, 4c and/or learning partial images which are created proceeding from the same sub-region of the initial image 4a, 4b, 4c, wherein at least one of the learning partial images is modified in relation to the sub-region of the initial image 4a, 4b, 4c in such a way that the learning partial images have different noise and/or different image intensity and/or different contrast and/or learning partial images of sub-regions originating from the same initial image 4a, 4b, 4c, wherein the similarity that is to be achieved between the particular learning partial images of the n-tuple is dependent on the spatial distance of the relevant sub-regions in the initial image 4a, 4b, 4c, wherein in particular learning partial images are considered to be all the more similar, the closer the relevant sub-regions are arranged to one another in the initial image 4a, 4b, 4c and/or creation of a compressed representation of the information contained in a partial image 3a, 3b, 3c, described by way of example in Bengio, Yoshua, Aaron Courville, and Pascal Vincent. "*Representation learning: A review and new perspectives.*" IEEE transactions on pattern analysis and machine intelligence 35.8 (2013): 1798-1828, Goodfellow, Ian, et al. "*Generative adversarial nets.*" Advances in neural information processing systems. 2014;

learning partial images from the same initial image 4a, 4b, 4c or from different initial images 4a, 4b, 4c which are to be considered similar on account of external features, such as text-based, numerical or semantic information, stored with the corresponding initial images 4a, 4b, 4c.

Following this learning phase, the projection of an indexing unit onto the partial images 3a, 3b, 3c of the data records 1a, 1b, 1c and/or onto a number of partial images of further data records is performed, and at least one feature vector is created accordingly for each of these partial images. The feature vectors 6a, 6b, 6c created in this way are stored in the data records in particular in a manner linked to the initial images.

A feature vector 6a shown in FIG. 1 by way of example for the data record 1a of the database 2 contains 18 entries and comprises a much lower number of entries than the three-dimensional image detail of a corresponding partial image 3a shows.

The individual initial images 4a, 4b, 4c or partial images 3a, 3b, 3c specified in order to create the database 2 can be provided optionally with additional information 5, wherein the additional information 5 is specified as text information and/or semantic information and/or numerical information. The additional information 5 may be medical information, for example. It can be specified for example that a portion of the mapped body parts comprises changes, what types of changes are concerned, or by which disease these changes have been caused. However, the additional information 5 can also be personal information, such as the age and sex of the patient. This additional information 5 can be stored optionally likewise in the data records 1a, 1b, 1c in the database 2. In order to store additional information 5 of this kind compactly in the database 2 and in order to display semantically relevant relationships, text information or numerical information is stored in the indexed data structure in the form of tags and/or semantic representations 7a, 7b, 7c and/or semantic information is stored in the index data structure in the form of semantic representations 7a, 7b, 7c.

In the example shown in FIG. 1 the entries in the medical records of the patient are available as additional information 5 for the data record 1a in the database 2. Here, instead of text-based contents of the medical records, semantic representations 7a of the entries in the medical records of the patient for age and sex and clinical picture are stored in the data record 1a in the database 2. The example concerns a 93-year-old male patient, diagnosed with lung cancer. In this case, number combinations are stored as semantic representations 7a: "82" represents the sex of the patient, "93" the age, and "16" the diagnosed disease. More complex information, such as more comprehensive descriptions in clinical observations, can be converted by self-trained neural networks, for example recurrent neural networks (RNNs), described by way of example in Sundermeyer, Martin, Ralf Schlüter, and Hermann Ney. "*LSTM neural networks for language modeling.*" Thirteenth Annual Conference of the International Speech Communication Association. 2012, or convolutional neural networks (CNNs) with attention mechanisms, described by way of example in Vaswani, Ashish, et al. "*Attention Is All You Need*" arXiv preprint arXiv:1706.03762 (2017), into semantic codes, optionally together with a weighting (for example "absent"/"mild"/ "possibly present"/"definitively present") and stored together therewith. Alternatively, entire paragraphs and reports can be displayed and stored by neural networks, for example paragraph vectors, as described by way of example in Dai, Andrew M., Christopher Olah, and Quoc V. Le. "*Document embedding with paragraph vectors.*" arXiv preprint arXiv:1507.07998 (2015).

Additional information 5 of this kind can optionally be utilized by the neural network in order to create the projection which maps partial images 3a, 3b, 3c onto feature vectors 6a, 6b, 6c. Here, the projection is created in such a way that learning partial images originating from initial images 4a, 4b, 4c or corresponding to partial images 3a, 3b, 3c associated with the same additional information 5 are specified as being similar.

In the shown example in FIG. 1, learning partial images in which the imaged lung tissue shows similar changes and which are associated with the same disease designation for example in the form of additional information 5, are specified for the learning of the projection or the creation of the feature vectors 6a, 6b, 6c. Partial images 3a, 3b, 3c, in which lung tissue having similar changes is imaged and the patient in question is suffering from a potentially similar disease, are thus mapped to similar feature vectors 6a, 6b, 6c.

Furthermore, the particular position of the partial images 3a, 3b, 3c of an initial image 4a, 4b, 4c in relation to the human body can be stored optionally in the data records 1a, 1b, 1c and the database 2. The information regarding the position of the partial images 3a, 3b, 3c can be used in particular by a neural network in order to learn a projection for finding body parts by means of feature vectors 6a, 6b, 6c of partial images 3a, 3b, 3c.

Search Query to the Database

In order to create a search request to the database 2, a query image 3' formed of at least one two-dimensional or higher-dimensional examination image 4' or in an examination image sequence is firstly selected by the user. Additional information 5 possibly available can be used additionally, however, by a search unit to create the search request, if such information is present.

Alternatively or additionally, text information, for example diagnosis text, numerical information, for example the age or age group of the patient, and/or semantic information, for example a disease, can also be specified by the user in order to create a search request. Here, the text information or numerical information can be converted by the search unit into tags and/or semantic representations 7a, 7b, 7c. A search is then performed for feature vectors 6a, 6b, 6c which display similar tags and/or semantic representations 7a, 7b, 7c.

For example, it is thus possible to create a search request for data records which for example are associated with a specific patient name or a specific disease. If, for example, a user creates a search request with "wrist fracture" as text information, the specified text information is converted into a semantic representation, in the example the number combination 53, and is transmitted to the database 2. In the example in FIG. 2, in this case the data record 1b, in which a corresponding semantic representation 7b is stored, is output as the result of the search.

In order to create a search request on the basis of image information to the database 2, one or more feature vectors 6' of the query image 3' is/are determined initially for the query image 3', as described above, in accordance with the learned projection. A search is then performed in the database 2 for data records 1a, 1b, 1c with feature vectors 6a, 6b, 6c, which lie in the vicinity of the feature vector 6' of the query image 3' on the basis of a predefined metric. Partial images 3a, 3b, 3c, which are optionally sorted and which look similar to the selection region, are output as the result of the search request, optionally together with or replaced by the data records 1a, 1b, 1c.

The sorting of the partial images of the result is based on the similarity of the corresponding feature vectors to the one or more feature vector(s) of the query image. The distances of the data records 1a, 1b, 1c from the query image and therefore an optional sorting can be determined for example by the accumulation of the distances of the result vectors for each data record by the number of result vectors per data record within a selected similarity threshold value by analysis of the spatial configuration of the partial images corresponding to the result vectors within the result data records by analysis of the additional information stored in the database for the result vectors.

Partial images 3a, 3b, 3c, which for example show similar disease pictures, can thus be found in the database 2 on account of the feature vectors 6a, 6b, 6c associated with them, without having to perform a time-consuming and processing-power-intensive search directly for partial images 3a, 3b, 3c. A comparatively quick search for feature vectors 6a, 6b, 6c which are similar to the feature vector 6' of the query image 3' is sufficient to find similar partial images 3a, 3b, 3c and the initial images 4a, 4b, 4c associated therewith. Furthermore, this approach makes it possible to find feature vectors 6a, 6b, 6c and corresponding partial images 3a, 3b, 3c which are indeed visually different, but are semantically relevant in accordance with the projection created by the training unit, since they are for example associated with the same disease picture.

Furthermore, criteria can be specified optionally by the user, for example in order to reduce the number of potential hits when searching a database 2. For example, when searching for similar feature vectors 6a, 6b, 6c in the database 2, search results can also be excluded on account of the tags and/or semantic representations 7a, 7b, 7c stored in the associated data records 1a, 1b, 1c in the database 2, wherein in particular search results can be excluded under criteria specified by the user for the tags and/or semantic representations 7a, 7b, 7c. For example, it is thus possible to search only for results of patients of the same sex and/or in the same age group.

A ranking of the determined data records 1a, 1b, 1c can be output optionally as a result of the search request. The determined data records 1a, 1b, 1c are ranked here by the search unit according to their similarity to or conformity with the tags and/or semantic representations 7a, 7b, 7c of the search request and/or according to their similarity, determined in particular by the distance of the relevant feature vectors 6a, 6b, 6c, to at least one query image 3' of the search request, and the ranking created in this way is displayed to the user.

The text information or numerical information stored in the relevant data records 1a, 1b, 1c in the form of tags and/or the semantic information stored in the form of semantic representations 7a, 7b, 7c can optionally be output as the result of the search request, and/or the tags of the partial images 3a, 3b, 3c similar to the selection region can be evaluated statistically. The statistical result thus obtained can then be output. This statistic can help, for example in the case of differential diagnosis, in grouping different disease pictures associated with visually similar signs or changes and in presenting these to the user. Furthermore, statistics regarding the frequency for example of male or female patients suffering from a specific disease or the frequency with which a specific age group is afflicted by a specific disease can be created easily for example by the user on the basis of the search results.

FIG. 2 shows a database 2 of a hospital having three data records 1a, 1b, 1c stored therein, which comprise information regarding patients or cases of disease. Each of the data records 1a, 1b, 1c comprises a feature vector 6a, 6b, 6c respectively, which in each case was created proceeding from a partial image 3a, 3b, 3c respectively, selected from initial images 4a, 4b, 4c systematically, for example by means of displacement of a pixel grid. The initial images 4a, 4b, 4c in FIG. 2 are three-dimensional computed tomography images, wherein the initial images 4a, 4c show images of lungs and the initial image 4b shows an image of a hand. The lobes of the lung shown in the initial images 4a, 4c each comprise changes to the lung tissue. The hand shown in the initial image 4b has a wrist fracture.

Each data record 1a, 1b, 1c in the database in FIG. 2 further comprises a semantic representation 7a, 7b, 7c respectively. In the example, number combinations represent the sex and the diagnosed disease, which in each case are noted in the medical records of the patient with whom the initial images 4a, 4b, 4c in question are associated. In the example, 82 represents "male", 89 "female", 16 the diagnosis "lung cancer" and 53 "wrist fracture".

In the example shown in FIG. 2, a first search request is made by a user to a database 2. A three-dimensional computed tomography image of a lung is specified as examination image 4'. In the examination image 4', a portion of the left lobe of the lung is selected by the user as query image 3', since this region of the lobe of the lung comprises changes. In order to verify his/her preliminary diagnosis of "lung cancer", the user would like to obtain, as the result of his/her search request to the database 2, data records which contain partial images of lung tissue comprising similar changes and which compare associated diagnoses with the diagnosis that he/she has made provisionally.

The query image 3' is used initially solely to create the first search request, wherein data records in the database 2 in which partial images similar to the query image 3' are stored in the database 2 should be determined. In order to create the search request, a feature vector 6' of the query image 3' is firstly created, as described above, in accordance with the learned projection proceeding from the query image 3', and is transferred as search request to the database 2, which is indicated schematically in FIG. 2 as a solid arrow in the direction of the database 2. Those data records of which the feature vectors are similar to the feature vector 6' of the query image 3' are then now determined in the database 2.

In the example shown in FIG. 2, the data records 1a and 1c are output as the result of the first search request; this circumstance is indicated by continuous arrows from the database 2. The feature vectors 6a, 6c of the data records 1a, 1c were created in each case proceeding from partial images 3a, 3c of an initial image 4a, 4c, which in each case show a three-dimensional computed tomography image of a lobe of a lung having similar changes to the query image 3'. The feature vector 6b stored in the data record 1b does not have sufficient similarity with the feature vector 6' of the query image 3', since the feature vector 6b was created on the basis of partial images 3b of an initial image 4b which shows a detail of a three-dimensional computed tomography image of a hand of a patient, and therefore is not output.

In addition, the semantic representations 7a, 7c stored in the data records 1a, 1c which in each case contain the number combination 16 for the diagnosis "lung cancer" are output. As the result of his/her search request, the user is thus now provided with the data records 1a, 1c comprising images of lung tissue having changes similar to those in the current patient and having the relevant diagnosis in each case, in this example "lung cancer", in order to verify his/her preliminary diagnosis.

In the example shown in FIG. 2, semantic representations 7' of the entries in the medical records of the patient whose examination image 4' forms the basis of the query are also available for the creation of the search requests. These semantic representations 7' in this case comprise the number combinations 82 for "male" and 16 for the preliminary diagnosis "lung cancer".

The user would now like to search selectively the data records belonging to male patients in whom lung cancer has been diagnosed and whose lung tissue demonstrates changes similar to those in the current patient. A second search request is therefore made to the database 2 by the user, in which request the search criteria "male" and "lung cancer" are specified by the user in addition to the query image 3'. In order to create the second search request, the query image 3' and the semantic representations 7' comprising 82 for "male" and 16 for "lung cancer" are therefore transmitted to the database 2, which is illustrated schematically in FIG. 2 as a dashed arrow in the direction of the database 2.

With the second search request, a search is now performed in the database 2 for data records having feature vectors that lie in the vicinity of the feature vector 6' of the query image 3' on the basis of a predefined metric, wherein data records whose semantic representations 7' do not include the number combination 82 for "male" and 16 for "lung cancer" are excluded.

In the example shown in FIG. 2, the data record 1*a* is output as the result of the second search request, this being indicated by a dashed arrow from the database 2. The data record 1*a* comprises a feature vector 6*a* which is similar to the feature vector 6' of the query image 3', and in addition the semantic representations 7*a* comprise the number combinations 82 for "male" and 16 for "lung cancer".

The data record 1*c* is not output as the result of the second request, although the feature vector 6*c* is similar to the feature vector 6' of the query image 3', since the semantic representation 7*c* comprises the number combination 89 for "female" and therefore does not match all criteria of the second search request. The data record 1*a*, which contains the images of the lungs of a male patient who has lung cancer, is thus available to the user for verification of his/her preliminary diagnosis.

Alternatively, the result of a first search request, for example "lung cancer", can be used in order to search for relevant content for example in reference databases, websites, databases containing scientific articles, or hospital information systems. Furthermore, due to the optional additional information of the data records regarding the position within the human body, information can be output in conjunction with the corresponding anatomical position ("lung bottom left") or the corresponding organ ("lower left lobe of the lung").

Alternatively, in order to create a search request for an examination image 4' or an examination image sequence of similar images by creation of a section, a dimension-reduced partial query image, which is also reduced in respect of its dimensions as appropriate, can be created, and this partial query image can be used for the search request. For example, higher-dimensional examination images 4' can thus be used to create a search request to a lower-dimensional database 2. A two-dimensional section for example from a three-dimensional computed tomography image can in this way be used as partial query image for a search request in a database 2 comprising data records with images from scientific articles.

Alternatively, in order to create a search request to a database 2, a two-dimensional query image 3' from a scientific article or from a website, or a portion thereof, can be specified by a user, for example. The database 2 to be queried can contain data records 1*a*, 1*b*, 1*c* comprising two-dimensional or three-dimensional initial and/or partial images.

A search request of this kind to a higher-dimensional database 2 proceeding from a lower-dimensional query image 3' is possible if the training unit, when creating projections in order to obtain feature vectors 6*a*, 6*b*, 6*c* from partial images 3*a*, 3*b*, 3*c*, was trained to map, in particular visually or semantically, similar partial images 3*a*, 3*b*, 3*c*, regardless of their partial image format, for example partial image dimension or size, onto similar feature vectors 6*a*, 6*b*, 6*c*.

Partial images 3*a*, 3*b*, 3*c*, which are mapped by a first projection, which was learned proceeding from learning partial images with a first dimension, to similar feature vectors 6*a*, 6*b*, 6*c* are thus also mapped by a second projection, which was learned proceeding from learning partial images with a second dimension, likewise to similar feature vectors 6*a*, 6*b*, 6*c*. Structures which for example are similar in a three-dimensional space are therefore also identified as being similar in a section.

Furthermore, a query image 3' of unknown position in the human body can optionally be specified by a user and transmitted as search request to the database 2. In this case the sought position in the human body is firstly determined, and a search is performed in the database 2 for feature vectors 6*a*, 6*b*, 6*c* of partial images 3*a*, 3*b*, 3*c* for which the same position in relation to the human body is stored in the respective data records 1*a*, 1*b*, 1*c*, or the position of which does not exceed a threshold value, specified by the user, for the distance from the sought position. Partial images 3*a*, 3*b*, 3*c*, which show a spatially similar detail of a human body as compared to the query image 3', are determined as the result of the search request.

The examination images 4' and/or examination image sequences and/or text information and/or numerical information and/or semantic information forming the basis of a search request can optionally be anonymized prior to the transmission of the search request by the user to the database 2. In this way, it can be ensured by the user that the personal data of a patient it is not transmitted to the database 2 when a search request is made. This can be achieved for example in accordance with the DICOM PS3.15 2013 anonymization guidelines.

Furthermore, in response to a search request of a user in the database 2, groups of partial images 3*a*, 3*b*, 3*c* and/or text information and/or numerical information and/or semantic information with similar feature vectors 6*a*, 6*b*, 6*c* can be created and output optionally, and as appropriate additional information 5 in respect of these groups, and/or adjacent groups of partial images 3*a*, 3*b*, 3*c* and/or text information and/or numerical information and/or semantic information with similar feature vectors 6*a*, 6*b*, 6*c* is determined and output, and as appropriate additional information 5 in respect of these groups is output.

Multi-Database Method (Cascade Search)

One embodiment of the invention offers the possibility of carrying out a multi-stage search method successively in a plurality of databases. Firstly, as described above, a first search request is transmitted to a database 2. The search results determined as the results of this first search request to the database 2, in particular partial images 3*a*, 3*b*, 3*c*, group information, text information, numerical information and/or semantic information, are then used to create at least one further search request, and this further search request is transmitted to at least one further database 2*a*.

In order to create the at least one further search request to the at least one further database 2*a*, further information output as the result of the first search request to the database 2, in particular output statistical results and/or initial images 4*a*, 4*b*, 4*c* and/or similar partial images 3*a*, 3*b*, 3*c*, can be used alternatively or additionally, wherein the dimension of the output initial images 4*a*, 4*b*, 4*c* and/or the output partial images 3*a*, 3*b*, 3*c* is reduced as appropriate for the search request in the at least one further database 2*a*, for example a literature database.

For example, it is thus possible, proceeding from determined three-dimensional partial images 3*a*, 3*b*, 3*c*, to create a further search request and to transmit this to a literature database containing only two-dimensional images, wherein for example data records containing two-dimensional images from scientific publications are output as the result.

Figure 3:
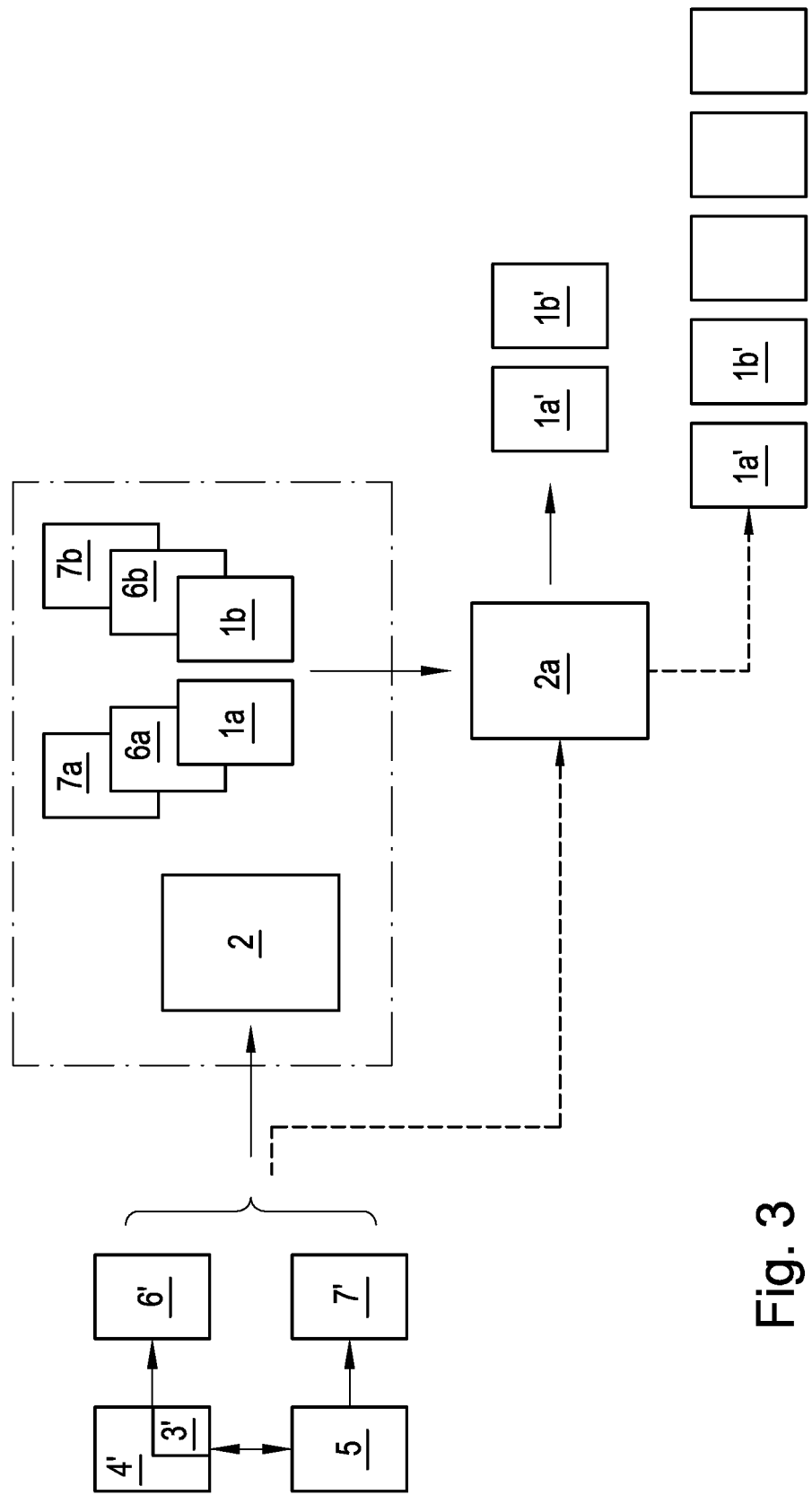
FIG. 3 shows schematically the sequence of a multi-database search process.

FIG. 3 shows schematically the sequence of a search method of this kind for searching the database 2 shown in FIG. 1 and FIG. 2, which database comprises data records 1*a*, 1*b*, 1*c* containing information determined within the scope of examinations performed on patients, and in a further database 2*a* which comprises further data records 1*a*', 1*b*' containing information from the specialist literature.

Firstly, a user, i.e. a doctor employed in the hospital, specifies an examination image 4' and a query image 3' selected therein in order to create a first search request to the database 2. In addition, the user in the shown example specifies additional information 5 as search criteria in order to create the first search request to the database 2, though this is by no means absolutely necessary. Proceeding from the query image 3', a feature vector 6' of the query image 3' is created after the projection created as described above, the additional information 5 is converted into semantic representations 7', and both are transmitted to the database 2 as first search request, which is indicated by a solid arrow.

As the result of the first search request, the data records 1*a*, 1*b* are output from the database 2 and comprise feature vectors 6*a*, 6*b* lying in the vicinity of the feature vector 6' of the query image 3' and comprise semantic representations 7*a*, 7*b* similar to the semantic representation 7' specified by the user.

In the example in FIG. 3 the data records 1*a*, 1*b* determined in the first search request to the database 2 are then used to create a further search request. To this end, sections are created through the three-dimensional partial images 3*a*, 3*b* and are used to create the further search request, which is transmitted to the further database 2*a*. The further data records 1*a*', 1*b*', which contain two-dimensional images from scientific publications, the feature vectors of which lie in the vicinity of the feature vectors 6*a*, 6*b* of the data records 1*a*, 1*b* determined as the result of the first search request, are output by the further database 2*a* as the result of the second search request.

A total of four data records is now available to the user in the example in FIG. 3, these data records being similar to the user's selected query image 3', wherein in the example the data records 1*a*, 1*b* of the database 2 contain three-dimensional partial images 3*a*, 3*b* or initial images 4A, 4*b* of patients in the hospital, and the further data records 1*a*', 1*b*' of the further database 2*a* contain two-dimensional images from a scientific specialist journal.

In addition, for example semantic representations 7*a*, 7*b* stored in the data records 1*a*, 1*b* determined in the first search request are also used in order to create the second search request. In this case data records which comprise semantic representations similar to the semantic representations 7*a*, 7*b* are determined in the further database 2*a*.

In the case of a multi-stage search method of this kind, individual data records 1*a*, 1*b*, 1*c* of the database 2 can optionally be used exclusively for the formation of a projection function, but are not made available to the user for inspection as results of queries.

This case is indicated in FIG. 3 by the dot-and-dash framing of the database 2. A user, for example a doctor with his/her own practice, does not have direct access to the data records 1*a*, 1*b*, 1*c* in the database 2, but can use the database 2 in order to create a multi-stage search request. In this case a query image 3' is selected by the user proceeding from the examination image 4' in order to create a first search request. A feature vector 6' of the query image 3' is determined for the query image 3' and is transmitted to the database 2.

As described previously, the data records 1*a*, 1*b* for which the partial images 3*a*, 3*b* look similar to the selected query image 3' are determined as the result. The data records 1*a*, 1*b*, however, are not shown to the user, and instead are used exclusively for the creation of a further search request, which is transmitted to the further database 2*a*. As the result to his/her search request, the user ultimately receives the further data records 1*a*', 1*b*' of the further database 2*a*, the partial images of which are similar to the selected query image 3' and the partial images 3*a*, 3*b* of the data records 1*a*, 1*b*.

The case that the user directly transmits a search request to the further database 2*a* is shown in FIG. 3 by the dashed arrows. In this case a search request is transmitted directly by the user to the further database 2*a*, and five data records are determined in the further database 2*a* and shown to the user as the result of the search request. The shown search results in this case also contain data records of less relevance, since in comparison to the multi-stage search the criterion of similarity to the data records 1*a*', 1*b*' of the database 2 is spared. This shows that a multi-stage search method delivers more precise search results.

When creating the database 2 in the data records 1*a*, 1*b*, 1*c*, size details regarding the pixel dimensions or voxel dimensions of the initial images 4*a*, 4*b*, 4*c* or partial images 3*a*, 3*b*, 3*c* can be stored optionally and/or the pixel dimensions or voxel dimensions for the initial images 4*a*, 4*b*, 4*c* or partial images 3*a*, 3*b*, 3*c* can be specified.

In order to specify the pixel dimensions or voxel dimensions, a search is performed for similar reference initial images or reference partial images, originating in particular from the same body part, with known pixel or voxel dimensions, and a scaling is then sought by image comparison, by means of which scaling the initial image or partial image can be brought optimally into conformity with the reference initial image or reference partial image, and, proceeding from this scaling and the known pixel dimensions or voxel dimensions of the reference initial image or reference partial image, the pixel dimensions or voxel dimensions of the initial image 4*a*, 4*b*, 4*c* or partial image 3*a*, 3*b*, 3*c* are determined and stored in the database 2.

Similarly, such a correspondence to a query image 3' for which no correspondence between pixel/voxel size and physical measurement units, such as mm, is known can be estimated as necessary by making a search request to the database 2 and using correspondences between pixel/voxel size and physical measurement unit of the reference initial images or reference partial images determined as the result of the search request in order to estimate the correspondence in the query image 3'.

The invention claimed is:

1. A method for creating a medical image database, comprising:
  a) creating, in the medical image database, data records which comprise a plurality of partial images of two-dimensional or higher-dimensional initial images of parts of the human body, wherein each of the partial images is a section or block within the initial image of the respective part of the human body;
  b) creating, from the partial images, a projection for obtaining feature vectors, wherein:
    the projection maps partial images from the plurality of partial images that are similar to one another to feature vectors with a short distance, and
    in order to prepare the execution of the projection, a neural network based on specified learning partial images from the plurality of partial images is created, wherein the data records or part of the data records are/is used by the neural network within the scope of a metric learning method to learn the projection and creation of the feature vectors from learning partial images or groups of learning partial images from the specified learning partial images and a specified similarity between the learning partial images, wherein the metric learning method is based on:

specification of n-tuples of sub-regions originating from a same initial image or groups of initial images as the learning partial images, wherein the similarity to be achieved between the learning partial images in question of the n-tuple is dependent on the spatial distance of the relevant sub-regions in the initial image, wherein the learning partial images are considered to be all the more similar, the closer the sub-regions in question are arranged to one another in the initial image, c) applying the projection to the partial images of the data records or to a number of further partial images of further data records, and accordingly obtain at least one feature vector for each of the partial images or further partial images, and d) storing the obtained at least one feature vectors in an index data structure of the medical image database;

wherein a position of each of the partial images of the initial image based on the human body is determined, and wherein information regarding the position of the partial images is used by a neural network to learn a projection for estimating the positions of partial images, wherein the projection is learned with a target function that, by mapping pairs or groups of partial images from the plurality of partial images, a spatial constellation of the pairs/groups before and after the projection is similar or wherein the projection is learned based on a known mapping of the partial images to positions wherein, in addition to the feature vectors, the information regarding the position of the partial images is stored in the database wherein, in the presence of a search request, a searched spatial position in the body is determined and the database is searched for feature vectors of partial images for which a same spatial position is stored in their data records or the spatial position of which does not exceed a threshold value, specified by a user, for a spatial distance from the searched position.

2. The method according to claim 1, wherein additional information is stored in the data records, wherein the additional information is specified as text information and/or semantic information and/or numerical information, and wherein, with the presence of text information or numerical information, the text information or numerical information is stored in the database in the form of tags and/or semantic representations.

3. The method according to claim 2, wherein the additional information is used by the neural network for creation of the projection, wherein the projection is created in such a way that the learning partial images which originate from the initial images or correspond to the partial images associated with the same additional information are specified as similar.

4. The method according to claim 1, wherein individual data records of the database are used exclusively for formation of a projection function, but are not provided to a user for inspection as results of queries.

5. The method according to claim 1, wherein size details regarding the pixel dimensions or voxel dimensions of the initial images or partial images are stored in the data records, or wherein for the initial images or partial images the pixel dimensions or voxel dimensions are predefined by searching for similar reference initial images or reference partial images, originating from a same body part, with known pixel or voxel dimensions a scaling is then sought by image comparison, by means of which scaling the initial image or partial image is brought optimally into conformity with a reference initial image or reference partial image, and proceeding from the scaling and the pixel dimensions or voxel dimensions of the reference initial image or reference partial image, the pixel dimensions or voxel dimensions of the initial image or partial image are determined and stored in the database.

6. A system for creating a medical image database, comprising a training unit and an indexing unit downstream of the training unit, wherein the training unit is designed, under a specification of data records in the medical image database, which data records comprise a plurality of partial images of two-dimensional or higher-dimensional initial images of parts of the human body, wherein each of the partial images is a section or block within the initial image of the respective part of the human body, to create a projection for obtaining feature vectors from the partial images, wherein:

the projection maps partial images from the plurality of partial images that are similar to one another to feature vectors with a short distance, and, for preparation of the execution of the projection, to create a neural network, based on specified learning partial images from the plurality of partial images, wherein the data records or part of the data records are/is used by the neural network within the scope of a metric learning method to learn the projection and creation of the feature vectors from learning partial images from the specified learning partial images and a specified similarity, between the learning partial images, wherein the metric learning method is based on:

specification of n-tuples of sub-regions originating from a same initial image as the learning partial images, wherein the similarity to be achieved between the learning partial images in question of the n-tuple is dependent on the spatial distance of the relevant sub-regions in the initial image, wherein the learning partial images are considered to be all the more similar, the closer the sub-regions in question are arranged to one another in the initial image, wherein the indexing unit is designed to apply the projection, created by the training unit, to the partial images of the data records or to a number of further partial images of further data records, and accordingly to obtain at least one feature vector for each of the partial images or further partial images, and to store the obtained at least one feature vectors in an index data structure of the medical image database;

wherein a position of each of the partial images of the initial image based on the human body is determined, and wherein information regarding the position of the partial images is used by a neural network to learn a projection for estimating the positions of partial images, wherein the projection is learned with a target function that, by mapping pairs or groups of partial images from the plurality of partial images, a spatial constellation of the pairs/groups before and after the projection is similar or wherein the projection is learned based on a known mapping of the partial images to positions wherein, in addition to the feature vectors, the information regarding the position of the partial images is stored in the database wherein, in the presence of a search request, a searched spatial position in the body is determined and the database is searched for feature vectors of partial images for which a same spatial position is stored in their data records or the spatial position of which does not exceed a threshold value, specified by a user, for a spatial distance from the searched position.

7. A method for creating a medical image database, comprising:
   a) creating, in the medical image database, data records which comprise a plurality of partial images of two-dimensional or higher-dimensional initial images of parts of the human body, wherein each of the partial images is a section or block within the initial image of the respective part of the human body;
   b) creating, from the partial images, a projection for obtaining feature vectors, wherein:
      the projection maps partial images from the plurality of partial images that are similar to one another to feature vectors with a short distance, and
      in order to prepare the execution of the projection, a neural network based on specified learning partial images from the plurality of partial images is created, wherein the data records or part of the data records are/is used by the neural network within the scope of a metric learning method to learn the projection and creation of the feature vectors from learning partial images or groups of learning partial images from the specified learning partial images and a specified similarity between the learning partial images, wherein the metric learning method is based on:
         specification of n-tuples of the learning partial images or the groups of learning partial images that are slightly shifted, rotated, skewed or stretched relative to one another and were created starting from the same initial image as similar,
   c) applying the projection to the partial images of the data records or to a number of further partial images of further data records, and accordingly obtain at least one feature vector for each of the partial images or further partial images, and
   d) storing the obtained at least one feature vectors in an index data structure of the medical image database.

8. A system for creating a medical image database, comprising a training unit and an indexing unit downstream of the training unit,
   wherein the training unit is designed,
      under a specification of data records in the medical image database, which data records comprise a plurality of partial images of two-dimensional or higher-dimensional initial images of parts of the human body, wherein each of the partial images is a section or block within the initial image of the respective part of the human body,
      to create a projection for obtaining feature vectors from the partial images, wherein:
         the projection maps partial images from the plurality of partial images that are similar to one another to feature vectors with a short distance, and,
         for preparation of the execution of the projection, to create a neural network, based on specified learning partial images from the plurality of partial images, wherein the data records or part of the data records are/is used by the neural network within the scope of a metric learning method to learn the projection and creation of the feature vectors from learning partial images from the specified learning partial images and a specified similarity, between the learning partial images, wherein the metric learning method is based on:
            specification of n-tuples of the learning partial images that are slightly shifted, rotated, skewed or stretched relative to one another and were created starting from the same initial image as similar,
   wherein the indexing unit is designed
      to apply the projection, created by the training unit, to the partial images of the data records or to a number of further partial images of further data records, and accordingly to obtain at least one feature vector for each of the partial images or further partial images, and
      to store the obtained at least one feature vectors in an index data structure of the medical image database.

9. A method for creating a medical image database, comprising:
   a) creating, in the medical image database, data records which comprise a plurality of partial images of two-dimensional or higher-dimensional initial images of parts of the human body, wherein each of the partial images is a section or block within the initial image of the respective part of the human body;
   b) creating, from the partial images, a projection for obtaining feature vectors, wherein:
      the projection maps partial images from the plurality of partial images that are similar to one another to feature vectors with a short distance, and
      in order to prepare the execution of the projection, a neural network based on specified learning partial images from the plurality of partial images is created, wherein the data records or part of the data records are/is used by the neural network within the scope of a metric learning method to learn the projection and creation of the feature vectors from learning partial images or groups of learning partial images from the specified learning partial images and a specified similarity between the learning partial images, wherein the metric learning method is based on:
         specification of n-tuples of the learning partial images or the groups of learning partial images that were created starting from the same sub-region of the initial image as similar, wherein at least one of the learning partial images is modified in relation to the sub-region of the initial image in such a way that the learning partial images have different noise and/or different image intensity and/or different contrast,
   c) applying the projection to the partial images of the data records or to a number of further partial images of further data records, and accordingly obtain at least one feature vector for each of the partial images or further partial images, and d) storing the obtained at least one feature vectors in an index data structure of the medical image database.

10. A system for creating a medical image database, comprising a training unit and an indexing unit downstream of the training unit, wherein the training unit is designed, under a specification of data records in the medical image database, which data records comprise a plurality of partial images of two-dimensional or higher-dimensional initial images of parts of the human body, wherein each of the partial images is a section or block within the initial image of the respective part of the human body, to create a projection for obtaining feature vectors from the partial images, wherein:

the projection maps partial images from the plurality of partial images that are similar to one another to feature vectors with a short distance, and, for preparation of the execution of the projection, to create a neural network, based on specified learning partial images from the plurality of partial images, wherein the data records or part of the data records are/is used by the neural network within the scope of a metric learning method to learn the projection and creation of the feature vectors from learning partial images from the specified learning partial images and a specified similarity, between the learning partial images, wherein the metric learning method is based on:

specification of n-tuples of the learning partial images that were created starting from the same sub-region of the initial image as similar, wherein at least one of the learning partial images is modified in relation to the sub-region of the initial image in such a way that the learning partial images have different noise and/or different image intensity and/or different contrast, wherein the indexing unit is designed to apply the projection, created by the training unit, to the partial images of the data records or to a number of further partial images of further data records, and accordingly to obtain at least one feature vector for each of the partial images or further partial images, and to store the obtained at least one feature vectors in an index data structure of the medical image database.

11. A method for creating a medical image database, comprising:

a) creating, in the medical image database, data records which comprise a plurality of partial images of two-dimensional or higher-dimensional initial images of parts of the human body, wherein each of the partial images is a section or block within the initial image of the respective part of the human body;

b) creating, from the partial images, a projection for obtaining feature vectors, wherein:

the projection maps partial images from the plurality of partial images that are similar to one another to feature vectors with a short distance, and in order to prepare the execution of the projection, a neural network based on specified learning partial images from the plurality of partial images is created, wherein the data records or part of the data records are/is used by the neural network within the scope of a metric learning method to learn the projection and creation of the feature vectors from learning partial images or groups of learning partial images from the specified learning partial images and a specified similarity between the learning partial images, wherein the metric learning method is based on:

specification of the learning partial images or the groups of learning partial images from the same initial image or from different initial images, which are considered to be similar due to external features, such as text-based, numerical or semantic information, stored with the corresponding initial images, c) applying the projection to the partial images of the data records or to a number of further partial images of further data records, and accordingly obtain at least one feature vector for each of the partial images or further partial images, and d) storing the obtained at least one feature vectors in an index data structure of the medical image database.

12. A system for creating a medical image database, comprising a training unit and an indexing unit downstream of the training unit, wherein the training unit is designed, under a specification of data records in the medical image database, which data records comprise a plurality of partial images of two-dimensional or higher-dimensional initial images of parts of the human body, wherein each of the partial images is a section or block within the initial image of the respective part of the human body, to create a projection for obtaining feature vectors from the partial images, wherein:

the projection maps partial images from the plurality of partial images that are similar to one another to feature vectors with a short distance, and, for preparation of the execution of the projection, to create a neural network, based on specified learning partial images from the plurality of partial images, wherein the data records or part of the data records are/is used by the neural network within the scope of a metric learning method to learn the projection and creation of the feature vectors from learning partial images from the specified learning partial images and a specified similarity, between the learning partial images, wherein the metric learning method is based on:

specification of the learning partial images or groups of learning partial images from the same initial image or from different initial images, which are considered to be similar due to external features, such as text-based, numerical or semantic information, stored with the corresponding initial images, wherein the indexing unit is designed to apply the projection, created by the training unit, to the partial images of the data records or to a number of further partial images of further data records, and accordingly to obtain at least one feature vector for each of the partial images or further partial images, and to store the obtained at least one feature vectors in an index data structure of the medical image database.

* * * * *